United States Patent [19]

Stephens et al.

[11] Patent Number: 4,604,995
[45] Date of Patent: Aug. 12, 1986

[54] SPINAL STABILIZER

[76] Inventors: David C. Stephens, 129 School Rd., Wilmington, Del. 19803; Craig D. Morgan, 902 Stuart Rd., Wilmington, Del. 19807

[21] Appl. No.: 595,259

[22] Filed: Mar. 30, 1984

[51] Int. Cl.⁴ .............................................. A61F 5/04
[52] U.S. Cl. .................. 128/69; 128/92 R; 128/92 D
[58] Field of Search .............. 128/69, 92 R, 92 D, 128/92 G

[56] References Cited

U.S. PATENT DOCUMENTS

| 3,565,066 | 2/1971 | Roaf et al. | 128/69 |
| 3,648,691 | 3/1972 | Lumb et al. | 128/92 D |
| 4,003,376 | 1/1977 | McKay et al. | 128/69 |
| 4,078,559 | 3/1978 | Nissinen | 128/69 |
| 4,429,690 | 2/1984 | Angelino-Pievani | 128/92 D |
| 4,444,181 | 4/1984 | Wevers | 128/92 D |
| 4,473,068 | 9/1984 | Oh | 128/92 R |

FOREIGN PATENT DOCUMENTS

| 59969 | 9/1954 | France | 128/92 R |
| 67552 | 3/1944 | Norway | 128/92 D |
| 536819 | 3/1977 | U.S.S.R. | 128/92 R |

OTHER PUBLICATIONS

LUQUE Segmental Spinal Instrumentation, by Edwardo R. Luque, M.D., Mexico City, Mexico.

Primary Examiner—Robert Peshock
Assistant Examiner—C. W. Shedd
Attorney, Agent, or Firm—Connolly and Hutz

[57] ABSTRACT

A surgical implant is used for imparting stability to the thoraco-lumbar spine by fixation of the implant to the spine with segmental spinal instrumentation. The implant comprises a unitary rod having a generally rectangular configuration formed by a pair of spaced apart branches, mirror image duplicated of one another and equally spaced apart along their entire length. A bight end piece interconnects the branch pair at the superior end portion thereof while a gate forming end piece closes the inferior end portion of the branch pair except for a small gate opening. The gate opening facilitates sublaminar wiring for fixation of the implant to the spine.

9 Claims, 4 Drawing Figures

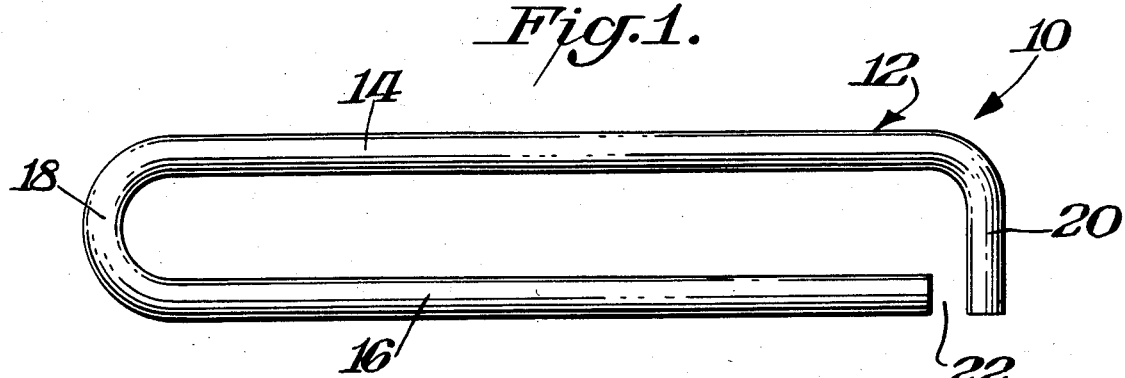
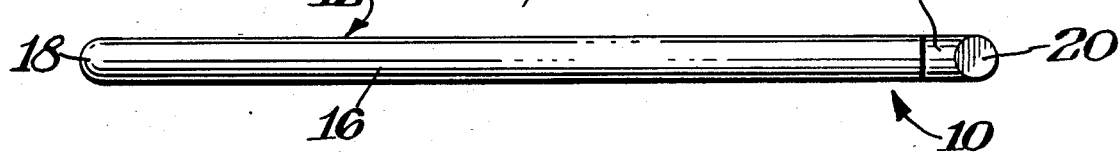
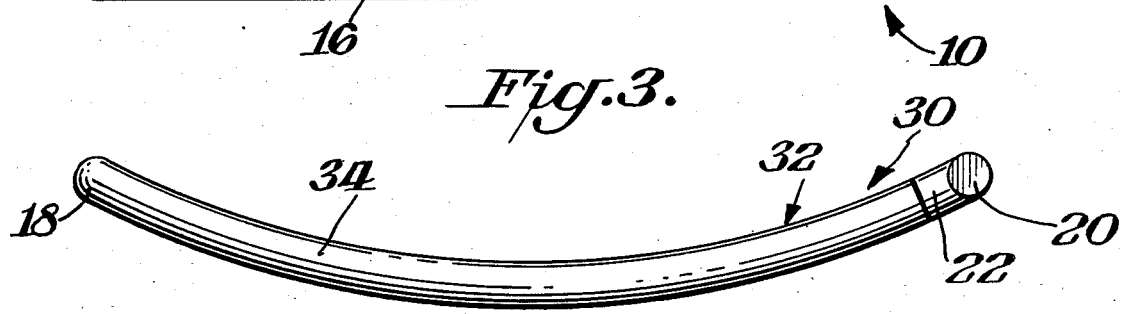
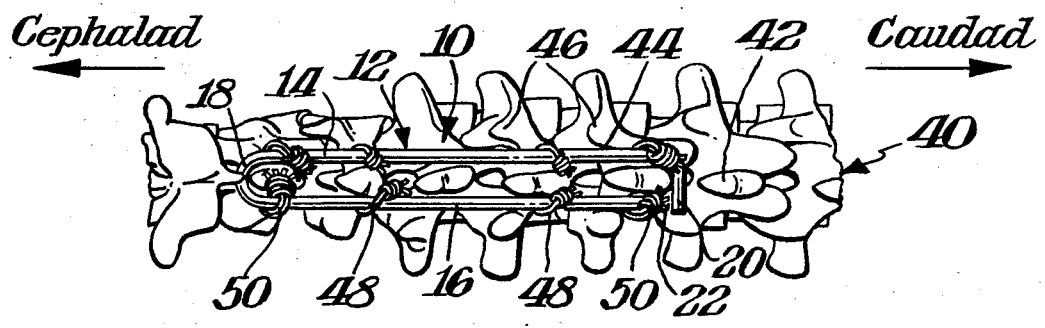

SPINAL STABILIZER

BACKGROUND OF THE INVENTION

The present invention relates to a surgical implant and method for imparting stability to the thoraco-lumbar spine.

Significant instability and deformity of the thoraco-lumbar spine may result from fracture dislocation as well as localized spinal involvement with malignant tumor. Also, surgical efforts to relieve spinal cord compression caused by tumor may increase such instability. Heretofore distraction and compression rods, such as the Harrington instrumentation, and more recently Luque rods with segmental spinal instrumentation, have been used for imparting stability to the damaged spine. Luque rods were originally designed for use with segmental spinal instrumentation in the correction of severe scoliotic curves over many spinal segments, normally numbering twelve or more, rather than more localized areas of six to ten segments.

SUMMARY OF THE INVENTION

Accordingly, it is an object of the present invention to provide a surgical implant that functions in a highly reliable and beneficial manner to impart stability to the thoraco-lumbar spine by fixation of the implant to the spine with segmental spinal instrumentation.

Another object of the present invention is a method for imparting stability to the spine which is relatively uncomplicated and which provides significant stability to a spine damaged by malignant disease or fracture.

In accordance with the present invention, a surgical implant imparts stability to the thoraco-lumbar spine by fixation of the implant to the spine with segmental spinal instrumentation. The implant comprises a unitary rod having a generally rectangular configuration formed by a pair of spaced apart branches substantially mirror image duplicates of one another and substantially equally spaced apart along their entire length. A bight end piece interconnects the branch pair at one end portion thereof while a gate forming end piece closes the other end portion of the branch pair except for a small gate opening which provides access to the space between the branch pair.

The surgical implant of the present invention may include unitary rod branches which are straight and substantially parallel to one another. Alternatively, these branches may be slightly curved in the same direction. Preferably the gate forming end piece is connected to only one of the branches and extends toward the other branch up to the small gate opening.

The branches of the unitary rod may be spaced apart about 2.5 cm. Moreover, each of the branches of the unitary rod has a length equivalent to the span of at least five vertebrae and may be from about 12 to 30 cm. in length. The rod is preferably fabricated from stainless steel having a circular cross section with a diameter of about 6 to 10 mm. Also the small gate opening may be about 3 mm.

The present invention also includes a method of imparting stability to the thoraco-lumbar spine through fixation of the implant to the spine with segmental spinal instrumentation.

BRIEF DESCRIPTION OF THE DRAWING

Novel features and advantages of the present invention in addition to those mentioned above will become obvious to those skilled in the art from a reading of the following detailed description in conjunction with the accompanying drawing wherein similar reference characters refer to similar parts and in which:

FIG. 1 is a top plan view of a surgical implant for imparting stability to the thoraco-lumbar spine, according to the present invention;

FIG. 2 is a side elevational view of the surgical implant shown in FIG. 1;

FIG. 3 is a side elevational view of a slightly modified surgical implant having curved rather than straight branches; and FIG. 4 is a diagrammatic plan view of a surgical implant fixed to the dorsal aspect of the spine with segmental spinal instrumentation, according to the present invention.

DETAILED DESCRIPTION OF THE INVENTION

Referring in more particularity to the drawing, FIGS. 1 and 2 illustrate a surgical implant 10 for imparting stability to the thoraco-lumbar spine by fixation of the implant to the spine with segmental spinal instrumentation, as explained more fully below. The implant comprises a unitary rod 12 having a generally rectangular configuration formed by a pair of spaced apart branches 14,16 which are mirror image duplicates of one another. As shown best in FIG. 1, branches 14,16 are equally spaced apart along their entire length. A bight end piece 18 interconnects the branch pair at the superior end portion thereof while a gate forming end piece 20 is connected to close the inferior end portion of the branch pair. A small gate 22 of about 3 mm. is provided for access to the space between the branch pair, as explained more fully below.

The branches 14,16 of the unitary rod 12 are straight and substantially parallel to one another. This structural feature is best shown in FIG. 2 of the drawing. Moreover, the gate forming end piece 20 is preferably connected to only one of the branches, such as 14, and extends toward the other branch 16 up to the small gate opening 22. End piece 20 is integrally joined to branch 14 by a right angle connection.

The branches of the unitary rod 12 are preferably spaced apart about 2.5 cm., this being sufficient for the passage of the spinous processes when the surgical implant 10 is instrumented to the spine. The length of each branch 14,16 extends from about 12 to 30 cm. Such length is sufficient whereby the implant extends a distance of two or three healthy spinal segments on each side of a fractured or malignant section. The exact length of the implant is determined at the time of implantation.

The unitary rod 12 is preferably fabricated from 316L stainless steel and the implant may be bent into its generally rectangular shape utilizing stainless steel rod having a circular cross section with a diameter of about 6 to 10 mm.

FIG. 3 illustrates another surgical implant 30 according to the present invention, which is identical to the implant 10 of FIGS. 1 and 2 except that the unitary rod 32 of implant 30 has branches 34 which are slightly curved in the same direction for correction and/or maintenance of lumbar lordosis and/or thoracic kyphosis as surgical anatomy dictates at the time of operation in addition to imparting stability to the spine. Otherwise the branches 34 are the same as branches 14,16 in that they are mirror image duplicates of one another and equally spaced apart along their entire length. Similar reference characters are used to identify the portions of surgical implant 30 which are the same as implant 10.

At operation a posterior approach is made to the spine 40 exposing the posterior elements including spinous processes 42, laminae 44 and facets 46, over an area of three segments above and three segments below the site of spinal instability. If a partial laminectomy with spinal canal decompression is to be performed, it is done at this time. The interspinous ligaments and ligamentum flavum are excised over a distance of two to three segments above and below the abnormal area. Sublaminar wires 48 are then passed beneath the laminae of each segment to be involved in the fixation of the surgical implant 10 or 30 to the spine.

The sublaminar wires 48 may comprise 16 gauge 316L stainless steel wire pre-bent to an appropriate length and looped to form double strands, each of about ten to twelve inches in length. The looped ends of the double wires are passed under and around the laminae and each looped end is then cut to form two separate wires. Each separate wire 48 is then provisionally hand-twisted on opposite sides of the spinous process 42. This procedure prevents those wire portions on the underside of the laminae from entering further into the spinal canal which might otherwise cause neurological damage. Two to three segments above and below the abnormal area are so wired, depending upon individual circumstances.

Laminectomy, if performed, is usually confined to one level. However, in cases with extensive tumor involvement, as many as three levels may be necessary. Hence, the total number of segments involved over which the surgical implant would be used is approximately five to ten segments. Also, at the inferior most segment near the gate forming end piece 20 and the superior most segment near the bight end piece 18, double wiring 50 is used, i.e. two sublaminar wires on either side of the midline of each lamina. If desired or necessary, double wiring may be used at all levels.

At this point, iliac bone graft is obtained from an adjacent iliac crest to achieve bony fusion of the spine over the area of instrumentation. The articular cartilage of the facet joints is excised on either side of the midline over the area to be instrumented and filled with plugs of cancellous bone.

A surgical implant 10 or a contoured implant 30 is then positioned next to the spine with the spinous processes 42 located in the space between the branches 14,16 of the unitary rod and the provisionally twisted wires on the outside of the branches. The bight end piece is located at the superior end of the site with the gate end piece at the inferior end. While FIG. 4 illustrates a surgical implant having straight and substantially parallel branches, a contoured implant may be used in those cases where it is necessary to accommodate lumbar lordosis and/or thoracic kyphosis. In these latter cases a French rod bending instrument is used to contour the implant to a shape such as shown in FIG. 3, for example.

Next, each sublaminar wire 48 is loosened from its provisionally twisted state and one limb thereof is passed to the inside of the unitary rod 12 through the access gate 22 and then hand-twisted with the other limb to fix the rod in place. While one limb of the wire could be passed under the branch of the rod, such procedure is not recommended since the portion of the wire on the underside of the lamina might enter further into the spinal canal causing neurological damage. Passing one limb of the wire through the gate 22 rather than under the branch eliminates this danger. Ultimately the wires are tightened over the branches of the unitary rod 12 to rigidly fix the rod to the spine. The ends of the wires are then cut and bent off and bone graft is placed over the area of the instrumented spine to be fused.

The surgical implant of the present invention is easy to insert comprising a single unitary rod with two parallel branches, one on either side of the midline of the spine. The implant achieves correction of translational malalignment associated with fractured deformity as it is wired to successive laminae above and below the site of instability. It is also significant that rod rotation and/or migration is prevented with the surgical implant herein fixed into position with segmental sublaminar wiring. There can be no rod rotation or migration due to the unitary design.

As explained above, the surgical implant herein is also used to correct and maintain lumbar lordosis or thoracic kyphosis by correctly contouring the branches 34 prior to fixation of the implant to the spine.

Overall, the rigid fixation to the spine may cause less fatigue forces on the sublaminar wires with fewer long term problems of wire breakage.

What is claimed is:

1. A surgical implant for imparting stability to the thoraco-lumbar spine by fixation of the implant to the spine with segmental spinal instrumentation, the implant comprising a unitary rod having a generally rectangular configuration formed by a pair of spaced apart branches substantially mirror image duplicates of one another and substantially equally spaced apart along their entire length, a bight end piece interconnecting the branch pair at one end portion thereof, and a gate forming end piece connected to close the other end portion of the branch pair except for a small gate opening to provide access to the space between the branch pair.

2. A surgical implant as in claim 1 wherein the branches of the unitary rod are straight and substantially parallel to one another.

3. A surgical implant as in claim 1 wherein the branches of the unitary rod are slightly curved in the same direction and by the same amount.

4. A surgical implant as in claim 1 wherein the gate forming end piece is connected to only one of the branches and extends toward the other branch up to the small gate opening.

5. A surgical implant as in claim 1 wherein the branches of the unitary rod are spaced apart about 2.5 cm.

6. A surgical implant as in claim 1 wherein each of the branches of the unitary rod are from about 12 to 30 cm. in length.

7. A surgical implant as in claim 1 wherein the unitary rod has a circular cross section with a diameter of about 6 to 10 mm.

8. A surgical implant as in claim 1 wherein the small gate opening is about 3 mm.

9. A surgical implant as in claim 1 wherein the unitary rod is stainless steel.

* * * * *